United States Patent
Liao et al.

(10) Patent No.: US 11,420,948 B2
(45) Date of Patent: Aug. 23, 2022

(54) SYNTHESIS METHOD FOR CARIPRAZINE

(71) Applicants: Zhejiang Huahai Pharmaceutical Co., Ltd, Zhejiang (CN); SHANGHAI SYNCORES TECHNOLOGIES INC. LTD., Shanghai (CN)

(72) Inventors: Wenjing Liao, Shanghai (CN); Jianfeng Ge, Zhejiang (CN); Jicheng Zhang, Shanghai (CN); Luning Huang, Shanghai (CN); Anping Tao, Shanghai (CN); Eric Gu, Shanghai (CN)

(73) Assignees: Zhejiang Huahai Pharmaceutical Co., Ltd., Zhejiang (CN); SHANGHAI SYNCORES TECHNOLOGIES INC. LTD., Shanghai (CN)

( * ) Notice: Subject to any disclaimer, the term of this patent is extended or adjusted under 35 U.S.C. 154(b) by 0 days.

(21) Appl. No.: 17/266,955

(22) PCT Filed: Aug. 6, 2019

(86) PCT No.: PCT/CN2019/099374
§ 371 (c)(1),
(2) Date: Feb. 8, 2021

(87) PCT Pub. No.: WO2020/042876
PCT Pub. Date: Mar. 5, 2020

(65) Prior Publication Data
US 2021/0300883 A1    Sep. 30, 2021

(30) Foreign Application Priority Data
Aug. 29, 2018 (CN) .......................... 201810993813.3

(51) Int. Cl.
*C07D 295/135*  (2006.01)
*C07B 43/06*  (2006.01)

(52) U.S. Cl.
CPC .......... *C07D 295/135* (2013.01); *C07B 43/06* (2013.01)

(58) Field of Classification Search
CPC .................................................. C07D 295/135
See application file for complete search history.

(56) References Cited

FOREIGN PATENT DOCUMENTS

| CN | 102256955 A | 11/2011 |
| CN | 105330616 A | 2/2016 |
| CN | 106518841 A | 3/2017 |
| CN | 106543039 A | 3/2017 |

OTHER PUBLICATIONS

Longji, et al. CN106543039 A, Mar. 29, 2017, English Translation.*
Bogdan Domanita. Methyltetrahydrofuran:simply better than tetrahydrofuran. The 11th Annual Green Chemistry and Engineering Conference (Jun. 26-29, 2007).*

* cited by examiner

*Primary Examiner* — Shawquia Jackson
(74) *Attorney, Agent, or Firm* — Umberg Zipser LLP; Jason Tejani

(57) ABSTRACT

The present application relates to a synthesis method for cariprazine, comprising performing an acylation reaction between a compound represented by formula (I) and dimethylcarbamoyl chloride in a reaction solvent in the presence of an aqueous solution of an inorganic base, so as to obtain the cariprazine compound represented by formula (II). The synthesis method overcomes defects in the prior art such as a long reaction time, large size impurities and the difficulty of purification, and provides a new method suitable for commercial production wherein the reaction is fast, impurity sizes are small, the product is easily purified, the purity of the product can reach 99.0% or more, and the yield is high.

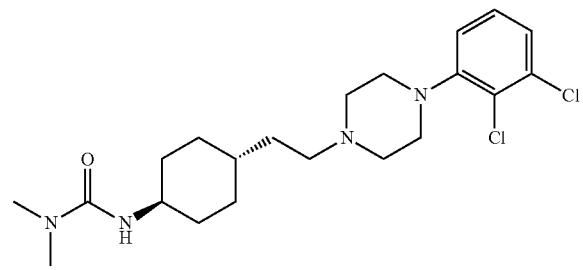

17 Claims, No Drawings

SYNTHESIS METHOD FOR CARIPRAZINE

The present application claims the priority of the Chinese patent application No. 201810993813.3, with the title of "SYNTHESIS METHOD FOR CARIPRAZINE", filed on Aug. 29, 2018 before the China National Intellectual Property Administration, which is hereby incorporated by reference in its entirety.

FIELD OF THE INVENTION

The present application belongs to the field of medical technology, and particularly relates to a synthesis method for cariprazine.

BACKGROUND OF THE INVENTION

Cariprazine, developed by original research Plc. Gedeon Richter (Gedeon Richter Ltd. Hungary), is a partial antagonist of dopamine D3 and D2 receptors and is used for the treatment of schizophrenia, bipolar disorder, bipolar depression and major depressive disorder.

The US FDA approved cariprazine (trade name: Vraylar®) capsules for the treatment of schizophrenia and bipolar disorder in adult patients on Sep. 17, 2015. The European Commission approved the new antipsychotic drug Cariprazine for the treatment of schizophrenia in adult patients on Jul. 13, 2017.

The structural formula of cariprazine (Compound II, CAS: 839712-12-8) is as follows:

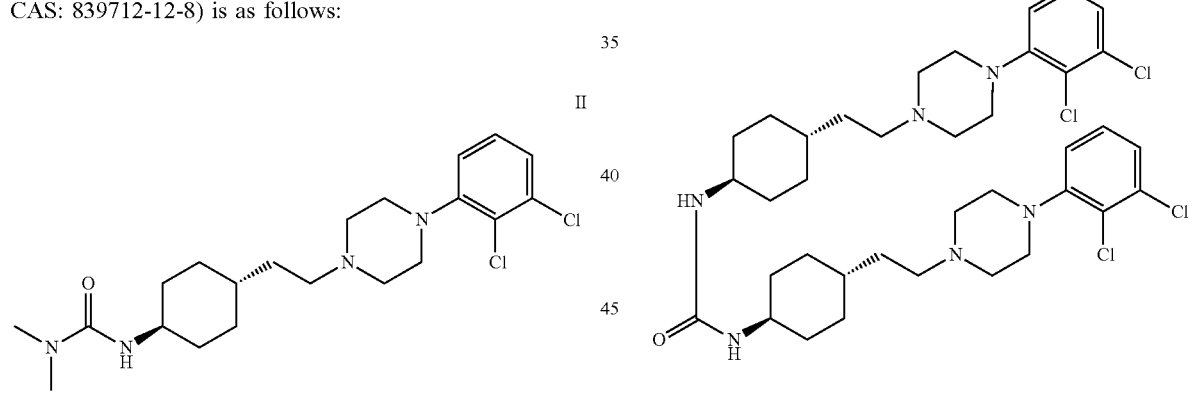

The existing synthetic routes of cariprazine mainly include:

1) WO 2005012266 reports the following synthesis method of cariprazine,

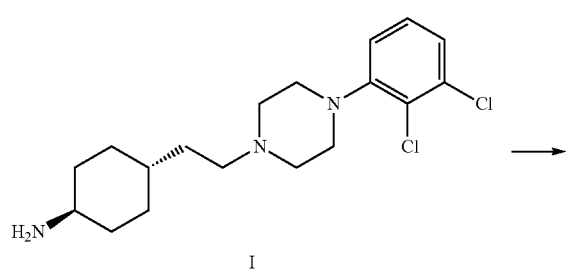

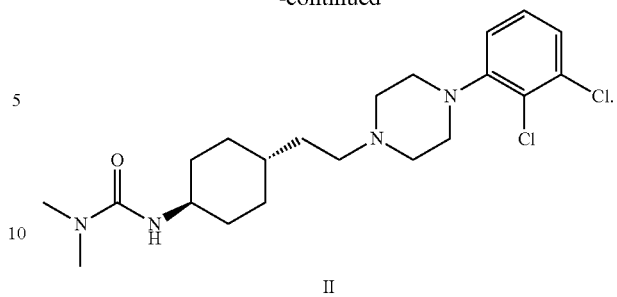

Cariprazine (compound II) is prepared by condensation of compound I with dimethylcarbamoyl chloride. This step requires stirring the reaction mixture at room temperature for 48 hours, with a yield of 65%.

2) CN105330616 discloses a method for preparing compound II from compound I:

A dichloromethane solution of dimethylcarbamoyl chloride is added dropwise to compound I, diisopropylethylamine and dichloromethane at low temperature, and it took 36 hours to react completely. The reaction yield at room temperature is 63.8%.

In summary, the prior art discloses a synthetic method for preparing compound II from compound I. The reaction takes 36 to 48 hours, and with the extension of reaction time, the di-substituted condensation impurity gradually increases from 0.1% to 0.6% after 18 hours. The structure of the double-condensation impurity is as follows:

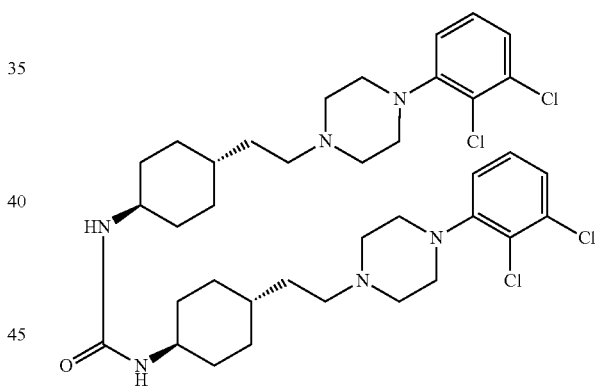

This impurity has poor solubility and is difficult to be purified; and the aforementioned synthesis method of cariprazine has low production efficiency and is not suitable for large-scale production. Therefore, there is still a need to develop a new synthetic method with simple operation, easy purification of products, and high chemical yield in the art.

SUMMARY OF THE INVENTION

The object of the present application is to provide a synthesis method of cariprazine, which is a new synthesis method wherein the reaction is fast, impurity sizes are small, the product is easily purified, and overcomes the defects in the prior art, such as long reaction time and difficulty in purification of impurities.

In order to achieve the above object, the present application adopts the following technical solutions:

The present application provides a method for synthesizing cariprazine represented by formula (II), comprising: in a reaction solvent, in the presence of an aqueous solution of an inorganic base, acylating the compound represented by formula (I) with dimethylcarbamoyl chloride to obtain cariprazine represented by formula (II), and the reaction formula is as follows:

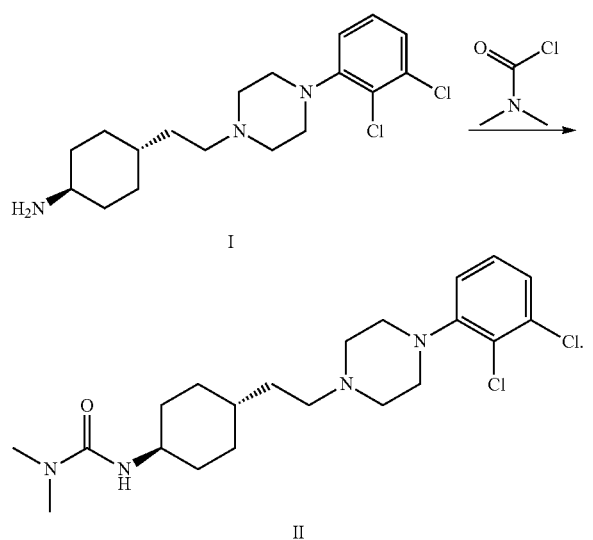

In the present application, the compound of formula (I) (also referred to as compound I) can be a compound with reagent grade or industrial grade purity; it can also be synthesized according to the prior art.

In some embodiments of the present application, the aqueous solution of the inorganic base is selected from the group consisting of one or at least two of NaOH aqueous solution, KOH aqueous solution, $Na_2CO_3$ aqueous solution, $K_2CO_3$ aqueous solution, $KHCO_3$ aqueous solution and $NaHCO_3$ aqueous solution, etc., preferably $Na_2CO_3$ aqueous solution or $K_2CO_3$ aqueous solution.

In some embodiments of the present application, a concentration of the inorganic base in the aqueous solution of the inorganic base is 5-30% by weight.

In some embodiments of the present application, the reaction solvent is a solvent that is immiscible with water, preferably one or at least two of dichloromethane, toluene, tetrahydrofuran and 2-methyltetrahydrofuran, etc.; more preferably dichloromethane or 2-methyltetrahydrofuran.

In some embodiments of the present application, a reaction temperature of the acylation reaction is 0 to 100° C. Under different reaction conditions, different reaction temperatures are selected to carry out within a temperature range based on the principle of not destroying other functional groups in the reactants and facilitating the reaction. In the present application, the reaction temperature is preferably 10 to 70° C., more preferably 15 to 30° C.

In some embodiments of the present application, a mole number of the inorganic base is greater than or equal to a sum of a mole number of the compound represented by formula (I) and a mole number of dimethylcarbamoyl chloride. More specifically, a ratio of the mole number of the inorganic base to the sum of the mole number of the compound represented by formula (I) and the mole number of dimethylcarbamoyl chloride is (2-6):1.

In some embodiments of the present application, the compound represented by formula (I) is added to the reaction solvent in the form of itself or salt thereof. In the specific implementation process, the salt of the compound represented by formula (I) can be selected from the group consisting of one or at least two of the dihydrochloride, sulfate, and dihydrobromide of the compound represented by formula (I); more preferably, the salt of the compound represented by formula (I) is dihydrochloride.

After adding the salt of the compound represented by formula (I) to the reaction solvent, the salt of the compound represented by the formula (I) is decomposed into the compound represented by the formula (I) under the action of the inorganic base, and then the compound is subjected to an acylation reaction with dimethylcarbamoyl chloride to obtain the cariprazine compound represented by formula (II).

In some embodiments of the present application, after completing the acylation reaction, the following steps further comprises: removing a water phase, adding a crystallization solvent to an organic phase to precipitate the cariprazine, and then filtering.

In some embodiments of the present application, before adding the crystallization solvent, if the reaction solvent in the organic phase is not dichloromethane, the reaction solvent in the organic phase is replaced with dichloromethane.

In some embodiments of the present application, the crystallization solvent is a low-polarity solvent such as n-heptane and/or cyclohexane, preferably n-heptane. In the present application, the crystallization solvent is also called an anti-solvent in the art.

The beneficial technical effects of the present application include: the cariprazine synthesis method provided by the present application has short reaction time, simple post-treatment, mild reaction conditions, significantly reduced double-condensation impurity content and a product purity of more than 99.0%. The total yield of the provided synthesis route is high. The synthesis method is not only suitable for small-scale laboratory preparation, but also suitable for large-scale industrial production.

DETAILED DESCRIPTION OF THE INVENTION

In order to make the technical problems solved by the present application, technical solutions and beneficial effects clearer, the following further describes the present application in combination with specific examples. In the following examples, unless otherwise specified, the specific conditions of the test method are usually implemented in accordance with conventional conditions or conditions recommended by the manufacturer; the raw materials and reagents are commercially available or prepared using public information.

In the following examples and comparative examples, the content of double-condensation impurity is specifically detected by HPLC (High Performance Liquid Chromatography). The specific detection conditions are as follows:

Detection method and conditions: Mobile Phase: 25 mmol ammonium acetate aqueous solution, acetonitrile; Detection Wavelength: 220 nm; Flow Rate: 1.0 mL/min; Chromatographic Column: C18 50*2.1 mm, 3.5 µm.

The retention time of double-condensation impurity: RT 17 min.

Example 1: Preparation of Cariprazine 20 g (56 mmol, 1.0 eq) of compound I, 300 ml of dichloromethane, and 60 ml of 20 wt % sodium hydroxide solution were added to a 1000 mL three-necked flask, and 9.1 g (84 mmol, 1.5 eq) of dimethylcarbamoyl chloride was added dropwise. Then the reaction mixture was stirred for 12 hours at 20-30° C. It was detected by HPLC that the raw materials had reacted completely, and the content of double-condensation impurity was 0.08%. After liquid separation of the reaction system and removal of a water phase, a dichloromethane phase was washed with water. Then the resultant was concentrated under reduced pressure to evaporate part of the dichloromethane. N-heptane was added to crystallize, then it was filtered, and the filter cake was dried to obtain 21.8 g of powdered solids (the cariprazine content was 99%, the purity was 99.5%, the double-condensation impurity content was 0.06%), with a yield of 90.9%.

Example 2: Preparation of Cariprazine 10 g (28 mmol, 1.0 eq) of compound I, 200 ml of dichloromethane, and 470 ml of 10 wt % potassium carbonate solution were added to a 1000 mL three-necked flask, and 4.5 g (42 mmol, 1.5 eq) of dimethylcarbamoyl chloride was added dropwise. Then the reaction mixture was stirred for 15 hours at 20-30° C. It was detected by HPLC that the raw materials had reacted completely. After liquid separation of the reaction system and removal of a water phase, a dichloromethane phase was washed with water. Then the resultant was concentrated under reduced pressure to evaporate part of the dichloromethane. N-heptane was added to crystallize, then it was filtered, and the filter cake was dried to obtain 10.7 g of powdered solids (the cariprazine content was 99%, the purity was 99.3%, the double-condensation impurity content was 0.09%), with a yield of 89.2%.

Example 3: Preparation of Cariprazine 20 g (56 mmol, 1.0 eq) of compound I, 500 ml of dichloromethane, 36 ml of 20 wt % sodium hydroxide solution and 500 ml of 10 wt % sodium carbonate were added to a 1000 mL three-necked flask, and 9.1 g (84 mmol, 1.5 eq) of dimethylcarbamoyl chloride was added dropwise. Then the reaction mixture was stirred for 13 hours at 15-25° C. It was detected by HPLC that the raw materials had reacted completely, and the content of double-condensation impurity was 0.07%. After liquid separation of the reaction system and removal of a water phase, a dichloromethane phase was washed with water. Then the resultant was concentrated under reduced pressure to evaporate part of the dichloromethane. N-heptane was added to crystallize, then it was filtered, and the filter cake was dried to obtain 22.3 g of powdered solids (the cariprazine content was 99%, the purity was 99.5%, the double-condensation impurity content was 0.06%), with a yield of 92.1%.

Example 4: Preparation of Cariprazine 10 g (28 mmol, 1.0 eq) of compound I, 400 ml of toluene, and 900 ml of 5 wt % potassium carbonate solution were added to a 1000 mL three-necked flask, and 4.5 g (42 mmol, 1.5 eq) of dimethylcarbamoyl chloride was added dropwise. Then the reaction mixture was stirred for 15 hours at 20-45° C. It was detected by HPLC that the raw materials had reacted completely. After liquid separation of the reaction system and removal of a water phase, a toluene phase was washed with water. Then the resultant was concentrated under reduced pressure to evaporate toluene and the toluene was replaced with dichloromethane. N-heptane was added to crystallize, then it was filtered, and the filter cake was dried to obtain 10.5 g of powdered solids (the cariprazine content was 99%, the purity was 99.5%, the double-condensation impurity content was 0.10%), with a yield of 87.5%.

Example 5: Preparation of Cariprazine 10 kg (28 mol, 1.0 eq) of compound I, 400 L of 2-methyltetrahydrofuran, and 400 L of 10 wt % sodium carbonate solution were added to a 1000 L reactor, and 4.5 Kg (42 mol, 1.5 eq) of dimethylcarbamoyl chloride was added dropwise. Then the reaction mixture was stirred for 14 hours at 20-50° C. It was detected by HPLC that the raw materials had reacted completely. After liquid separation of the reaction system and removal of a water phase, a 2-methyltetrahydrofuran phase was washed with water. Then the resultant was concentrated under reduced pressure to evaporate 2-methyltetrahydrofuran and the 2-methyltetrahydrofuran was replaced with dichloromethane. N-heptane was added to crystallize, then it was filtered with suction, and the filter cake was dried to obtain 10.2 kg of powdered solid (the cariprazine content was 99%, the purity was 99.2%, the double-condensation impurity content was 0.10%), with a yield of 85.0%.

Example 6: Preparation of Cariprazine 1 kg (2.33 mol, 1.0 eq) of dihydrochloride of compound I, 20 kg of dichloromethane, and 15 kg of water to a 100 L reactor, and then 20 L of 10 wt % sodium hydroxide solution was added dropwise. 0.375 Kg (3.49 mol, 1.5 eq) of dimethylcarbamoyl chloride was added dropwise. Then the reaction mixture was stirred for 13 hours at 20-50° C. It was detected by HPLC that the raw materials had reacted completely. After separating the reaction system, washing it with water three times and removing the water phase. N-heptane was added to crystallize, then it was filtered, and the filter cake was dried to obtain 0.834 kg of powdered solids (the cariprazine content was 99.1%, the purity was 99.3%, the double-condensation impurity content was 0.09%), with a yield of 83.0%.

Comparative Example: Preparation of Cariprazine 17.8 g of compound I (50 mmol, 1.0 eq), 300 ml of dichloromethane, 10.0 g of diisopropylethylamine (80 mmol, 1.6 eq) were added to a 1000 mL three-necked flask, and then 0.64 g (60 mmol, 1.2 eq) of dimethylcarbamoyl chloride was added dropwise. The reaction mixture was stirred for 12 hours at 20-30° C., and it was detected that the content of remaining raw materials were 25% and the content of double-condensation impurity was 0.23%. After further stirring for 36 hours, it was detected by HPLC that the raw materials had reacted completely, and the content of double-condensation impurity was 0.62%. The reaction solution was washed with 100 ml of 1% ammonia water and 100 ml of saturated brine successively. Then the resultant was dried over anhydrous sodium sulfate and concentrated under reduced pressure. The remainder was crystallized with n-heptane to obtain 14.1 g of white powdered solids cariprazine (II) (the content was 98%, the purity was 98.9%, the double-condensation impurity content was 0.56%), with a yield of 64.6%. After crystallization with ethyl acetate/n-heptane and methanol/dichloromethane system for several times, the content of double-condensation impurity was decreased to 0.15%, and 4.57 g of cariprazine (II) was obtained as off-white solids with a yield of 20.5%.

The purpose of the above-mentioned examples is to explain the substantive contents of the present application, but it does not limit the protection scope of the present application. Those skilled in the art should understand that the technical solution of the present application can be modified or equivalently replaced without departing from the essence and protection scope of the technical solution of the present application.

The invention claimed is:

1. A method of synthesizing cariprazine represented by formula (II), comprising: in a reaction solvent, in the presence of an aqueous solution of an inorganic base, acylating a compound represented by formula (I) with dimethylcarbamoyl chloride to obtain cariprazine represented by formula (II), as shown in the reaction formula:

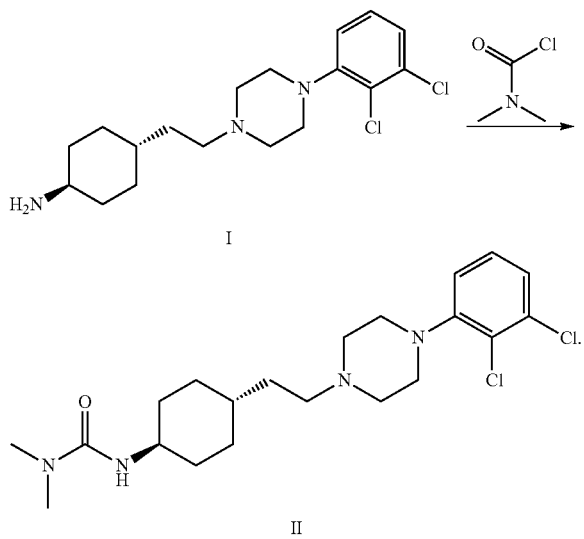

wherein the aqueous solution of the inorganic base is $Na_2CO_3$ aqueous solution or $K_2CO_3$ aqueous solution.

2. The method according to claim 1, wherein the inorganic base has a concentration of 5-30% by weight in the aqueous solution of the inorganic base.

3. The method according to claim 1, wherein the reaction solvent is a solvent that is immiscible with water.

4. The method according to claim 3, wherein the reaction solvent is one or at least two selected from the group consisting of dichloromethane, toluene, tetrahydrofuran and 2-methyltetrahydrofuran.

5. The method according to claim 3, wherein the reaction solvent is dichloromethane or 2-methyltetrahydrofuran.

6. The method according to claim 1, wherein a reaction temperature of the acylation reaction is 0-100° C.

7. The method according to claim 6, wherein the reaction temperature of the acylation reaction is 10-70° C.

8. The method according to claim 6, wherein the reaction temperature of the acylation reaction is 15-30° C.

9. The method according to claim 1, wherein a ratio in mole of the inorganic base to a sum of the compound represented by formula (I) and dimethylcarbamoyl chloride is greater than or equal to 1.

10. The method according to claim 1, further comprising: after completing the acylation reaction, removing a water phase, adding a crystallization solvent to an organic phase to precipitate cariprazine, and then filtering.

11. The method according to claim 10, wherein, before adding the crystallization solvent, if the reaction solvent in the organic phase is not dichloromethane, the reaction solvent in the organic phase is replaced with dichloromethane.

12. The method according to claim 10, wherein the crystallization solvent is n-heptane and/or cyclohexane.

13. The method according to claim 1, wherein the compound represented by formula (I) is added to the reaction solvent in the form of itself or salt thereof.

14. The method according to claim 9, wherein a ratio in mole of the inorganic base to the sum of the compound represented by formula (I) and dimethylcarbamoyl chloride is 2-6:1.

15. The method according to claim 12, wherein the crystallization solvent is n-heptane.

16. The method according to claim 13, wherein the salt of the compound represented by formula (I) is one or at least two selected from the group consisting of the dihydrochloride, sulfate, and dihydrobromide of the compound represented by formula (I).

17. The method according to claim 13, wherein the salt of the compound represented by formula (I) is dihydrochloride of the compound represented by formula (I).

* * * * *